United States Patent
Bates et al.

(10) Patent No.: US 10,350,371 B2
(45) Date of Patent: Jul. 16, 2019

(54) PEN NEEDLE ASSEMBLY

(71) Applicant: Becton, Dickinson and Company, Franklin Lakes, NJ (US)

(72) Inventors: James Bates, Sparta, NJ (US); Robert Banik, Edgewater, NJ (US); Abhijitsinh S. Raj, Morris Plains, NJ (US); Joshua Herr, Cary, NC (US); Joseph Brizzolara, Vermillion, OH (US); Amit Limaye, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 415 days.

(21) Appl. No.: 14/655,710

(22) PCT Filed: Dec. 20, 2013

(86) PCT No.: PCT/US2013/076787
§ 371 (c)(1),
(2) Date: Jun. 25, 2015

(87) PCT Pub. No.: WO2014/105667
PCT Pub. Date: Jul. 3, 2014

(65) Prior Publication Data
US 2015/0328412 A1   Nov. 19, 2015

Related U.S. Application Data

(60) Provisional application No. 61/746,109, filed on Dec. 26, 2012, provisional application No. 61/746,108, (Continued)

(51) Int. Cl.
*A61M 5/34* (2006.01)
*A61M 5/32* (2006.01)
(Continued)

(52) U.S. Cl.
CPC ............ *A61M 5/346* (2013.01); *A61M 5/002* (2013.01); *A61M 5/329* (2013.01);
(Continued)

(58) Field of Classification Search
CPC ............ A61M 5/34; A61M 2025/0008; A61M 5/3293; A61M 5/343; A61M 5/345;
(Continued)

(56) References Cited

U.S. PATENT DOCUMENTS 1,746,009 A    2/1930  Mulford
2,569,901 A *  10/1951 Nicolas ................. A61M 5/178
                                                          604/117

(Continued)

FOREIGN PATENT DOCUMENTS

CN    100551455 C    10/2009
JP    H08-52213      8/1994
(Continued)

*Primary Examiner* — Bradley J Osinski
*Assistant Examiner* — Nilay J Shah
(74) *Attorney, Agent, or Firm* — Dickinson Wright PLLC

(57) ABSTRACT

A pen needle is provided with a plastic non-patient end. Since the non-patient end needle does not contact the patient, the needle can be formed with a larger diameter, permitting more secure attachment to a medication pen and greater medication flow from the cartridge through the cannula. In addition, a two-part hub construction comprising a needle bearing sub assembly and an adapter for attachment to the pen body may be used to lower materials volume and costs, and reduce sharps disposal. In embodiments, a hub according to the invention may be provided with a shield that provides an audible and/or tactile indication when full penetration depth of the needle is achieved. Windows on the shield may reveal a color band on the hub at the full-penetration depth position to provide the user with a visual indication that the pen needle has been used.

6 Claims, 6 Drawing Sheets

Related U.S. Application Data filed on Dec. 26, 2012, provisional application No. 61/746,103, filed on Dec. 26, 2012.

(51) Int. Cl.

| | | |
|---|---|---|
| *A61M 5/00* | (2006.01) | |
| *A61M 5/46* | (2006.01) | |
| *A61M 5/50* | (2006.01) | |
| *A61B 5/15* | (2006.01) | |

(52) U.S. Cl.
CPC ........ *A61M 5/3286* (2013.01); *A61M 5/3293* (2013.01); *A61M 5/345* (2013.01); *A61M 5/347* (2013.01); *A61M 5/46* (2013.01); *A61M 5/5086* (2013.01); *A61B 5/15019* (2013.01); *A61B 5/150175* (2013.01); *A61B 5/150183* (2013.01); *A61B 5/150198* (2013.01); *A61M 2205/581* (2013.01); *A61M 2205/582* (2013.01); *A61M 2205/583* (2013.01); *A61M 2205/584* (2013.01); *A61M 2206/00* (2013.01)

(58) Field of Classification Search
CPC ...... A61M 5/347; A61M 5/46; A61M 5/5086; A61M 2205/581; A61M 2205/582; A61M 2205/583; A61M 2205/584; A61M 5/321; A61M 5/322; A61B 5/150175; A61B 5/150183; A61B 5/15019; A61B 5/150198
See application file for complete search history.

(56) References Cited

U.S. PATENT DOCUMENTS

| | | |
|---|---|---|
| 3,974,832 A | 8/1976 | Kruck |
| 5,042,977 A | 8/1991 | Bechtold et al. |
| 5,250,026 A * | 10/1993 | Ehrlich ............. A61M 37/0069 604/117 |
| 5,829,589 A | 11/1998 | Nguyen et al. |
| 6,171,276 B1 | 1/2001 | Lippe et al. |
| 6,190,348 B1 * | 2/2001 | Tiemann .................. A61F 13/26 604/15 |
| 9,445,838 B2 | 9/2016 | Wei et al. |
| 2002/0029059 A1 | 3/2002 | Purcell |
| 2002/0052580 A1 | 5/2002 | Ooyauchi |
| 2010/0286611 A1 | 11/2010 | Schraga |
| 2010/0324485 A1 | 12/2010 | Cowe |
| 2011/0048540 A1* | 3/2011 | Stroup ............. A61M 5/16881 137/1 |
| 2011/0152822 A1 | 6/2011 | Drunk et al. |
| 2011/0160675 A1 | 6/2011 | Ruan et al. |
| 2011/0230827 A1 | 9/2011 | Mori et al. |
| 2012/0226233 A1 | 9/2012 | Schraga |
| 2012/0226239 A1 | 9/2012 | Green |

FOREIGN PATENT DOCUMENTS

| | | |
|---|---|---|
| JP | 2002-159576 | 12/2000 |
| JP | 2007-528274 A | 10/2007 |
| JP | 2012-120844 | 6/2012 |
| JP | 2012-519546 A | 8/2012 |
| WO | WO-2011/034576 A1 | 3/2011 |
| WO | WO-20111/101351 | 8/2011 |
| WO | WO-2011/146042 A1 | 11/2011 |

* cited by examiner

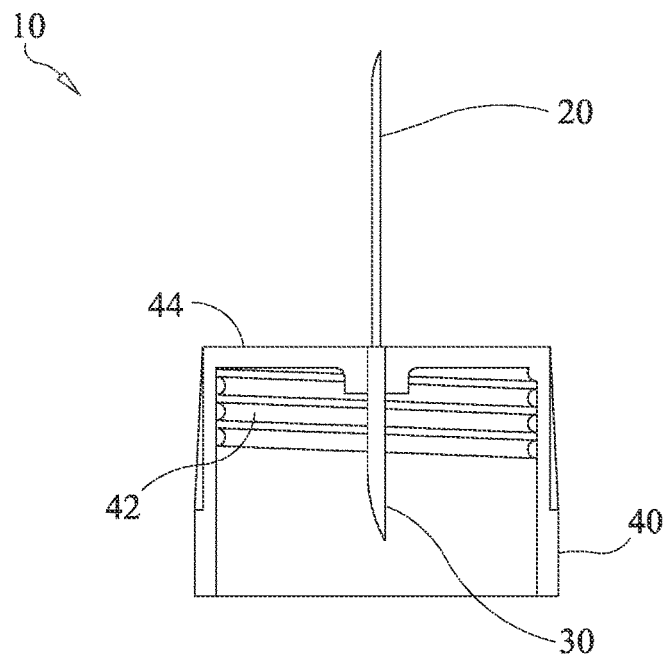
FIG. 1
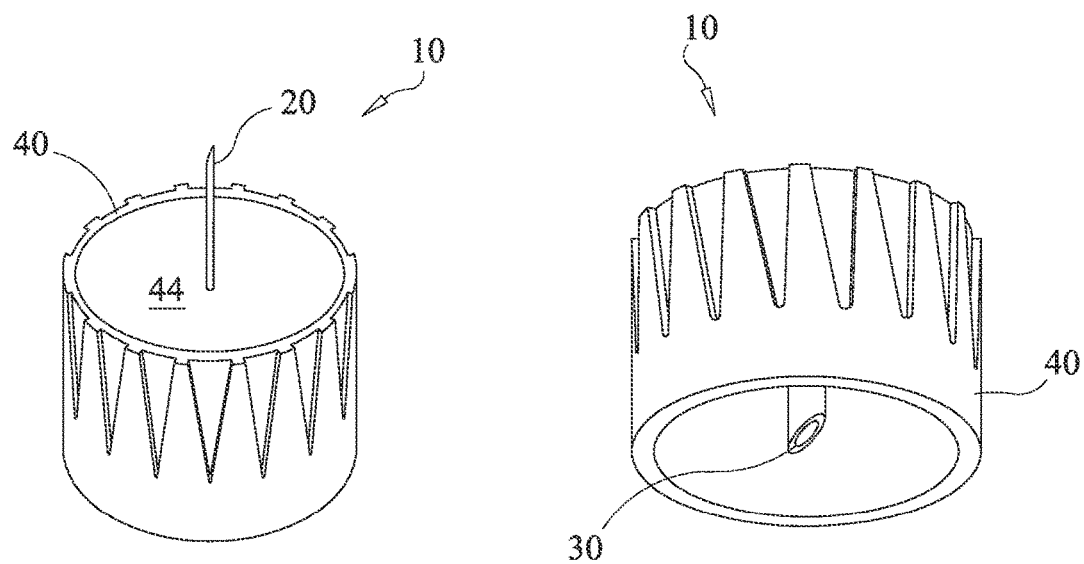
FIG. 2                    FIG. 3

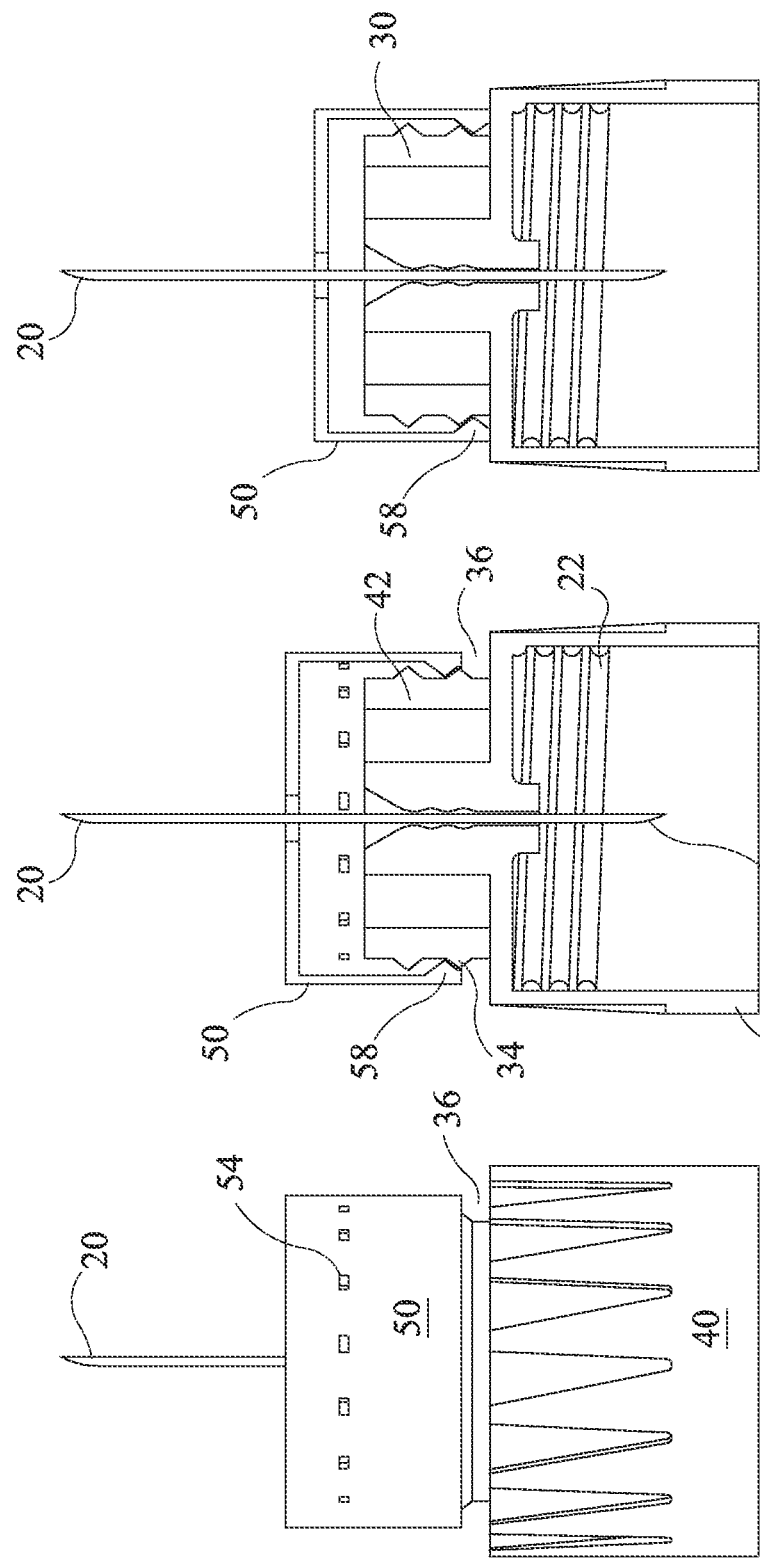

PEN NEEDLE ASSEMBLY

This application claims the benefit of U.S. Provisional Application No. 61/746,108, filed Dec. 26, 2013; U.S. Provisional Application No. 61/746,109, filed Dec. 26, 2013; and U.S. Provisional Application No. 61/746,103, filed Dec. 26, 2013, all of which are incorporated by reference.

BACKGROUND OF THE INVENTION

Field of the Invention

The invention is directed to a pen needle which may be installed on a drug delivery device, such as a medication pen, including modifications that make the pen needle more cost effective and user friendly.

Description of the Related Art

Pen needles are widely used in medication delivery systems for self-administered injectable drugs. The pen needles that are commonly used have a single stainless steel cannula extending through the needle-bearing hub. The non-patient end of the needle pierces the closure of the drug storage compartment of the medication pen while the patient end of the needle is adapted for insertion into the patient's tissue. Thus, in the conventional pen needle, since a single cannula is used, both ends of the cannula have the same inner and outer diameter. A problem exists in that thinner gauge needles which may be preferred for patient comfort do not reliably pierce the septum of the medication compartment when the pen needle is installed on the medication pen.

Another drawback of the commonly available pen needles is that they do not provide the user with an indication that the needle has reached the optimal penetration depth. The user relies on subjective sensation of pain when performing an injection to determine the depth of penetration, which may result in too much or too little penetration. An injection that is too deep may cause unnecessary pain when the needle is pressed too hard against the body, while an injection that is not deep enough may result in improper dosing. Thus, there is a need for pen needles that provide penetration depth indication.

These and other drawbacks of the prior art are achieved according to the present invention as described in the following specification and claims.

SUMMARY OF THE INVENTION

The inventors herein have explored ways to make lower cost pen needles with reduced materials usage while retaining the popular functional features of current products. In one aspect, the disclosure pertains to a pen needle which has a plastic non-patient end cannula which may be molded in one piece with the hub. This affords the advantage that a larger diameter cannula may be used on the non-patient end to provide strength to pierce the septum of the medication cartridge, while a lighter gauge stainless steel needle is used on the patient end for increased patient comfort during an injection.

In another aspect, the invention is directed to a pen needle having a needle-bearing hub with a two part construction, including an adapter which is attached to the medication delivery device for repeated use, and a single use needle. The volume of disposable needle components is significantly reduced compared to a conventional pen needle in which the entire hub is disposable.

In still another aspect, the disclosure pertains to a pen needle which provides an audible, tactile, and/or visual indication of penetration depth so that the user knows when full injection penetration depth has been achieved. The penetration depth indication is provided by a movable shield that may be incorporated with the above described hub designs with a plastic non-patient end cannula and/or two-piece hub.

Thus, in one aspect the invention is a disposable pen needle, comprising: a hub adapted for attachment to an injection pen body having a plastic non-patient end needle, and a metal patient end cannula attached to the hub.

In embodiments, the patient end cannula according to the invention is 33 gauge or smaller and the non-patient end needle is larger gauge that the patient end needle. However, the invention is not limited to a 33 gauge patient end needle.

In another aspect, the pen needle according to the invention comprises a hub which is split in two, comprising: a reusable adapter configured for attachment to a distal end of a medication pen, having a proximal needle for accessing the interior of the pen and a fitting on the distal side for mating with a patient end needle assembly. The disposable patient-end needle assembly has a base configured for mating with the fitting on the distal side of the adapter and a patient-end needle extending from a distal end of the base.

In embodiments according to this aspect of the invention, the pen needle further comprises a cover on the needle assembly, mating with the base and forming a sterile enclosure around the needle prior to use and forming a disposal-safe assembly after use.

In other embodiments according to this aspect of the invention, the adapter is provided with a valve or septum to prevent fluid leakage from the interior of the medication pen when the needle assembly is removed. Alternatively, a separate cap may be provided for the adapter to cover the orifice on the distal end of the adapter when the needle assembly is not present.

In still another aspect, the invention is a pen needle that provides audible and/or tactile indication of penetration depth. In embodiments, the pen needle comprises a needle-bearing hub adapted for attachment to a medication pen body, having a central post extending distally from a main body portion of the hub. The main body portion of the hub is wider than the post. The post is provided with a radially outwardly projecting member and at least one recess adjacent the main body portion of the hub. A cup (sometimes referred to as the "shield") is radially situated around the post and has a hole to allow passage of the needle. The cup has a skin contact surface on a distal side thereof and a sidewall extending proximally from the skin contact surface. The sidewall has an inwardly projecting member engaging the outwardly projecting member on the post. The cup is movable from a first position, in which the inwardly projecting member is on a distal side of the outwardly projecting member on the post, and a second position, in which the inwardly projecting member on the cup engages a recess adjacent the main body portion of the hub. Movement of the cup from the first position to the second position creates an audible and/or tactile indication from the engagement of the inwardly projecting member on the cup and the recess adjacent the main body portion of the hub to indicate full penetration depth of the needle. An optimal patient end needle length is predetermined for the intended use of the medication pen.

In embodiments, a central post is not provided on the hub and the cup is received over the widest portion of the hub. In this case, an outwardly projecting member may be provided on a radially outward surface on the side of the widest portion of the hub to engage an inwardly projecting member on the cup.

In still another aspect, a pen needle according to the invention provides a visual indication that optimal penetration depth has been achieved. In this aspect, the cup is provided with at least one window, and a color indicator is provided on the hub which is not visible through the window in the first position, but is visible through the window in the second position, so that a user knows that a predetermined injection depth has been achieved.

Visual indication may be combined with audible/tactile indication, and penetration depth indication in general may be combined with the plastic non-patient end needle and the two-piece hub embodiments described above.

BRIEF DESCRIPTION OF THE DRAWINGS

FIG. 1 is a cross sectional view of a pen needle having a plastic non patient end needle according to an embodiment of the invention.

FIG. 2 is an isometric view of a pen needle according to the embodiment of FIG. 1.

FIG. 3 is an isometric view of the pen needle according to the embodiment of FIG. 1 showing the non-patient cannula.

FIG. 6 is a side view of the assembly of FIG. 5 in a state prior to reaching full penetration depth.

FIG. 7 is a cross sectional side view of the assembly of FIG. 5 prior to reaching full penetration depth.

FIG. 8 is a cross sectional side view of the assembly of FIG. 6 at full penetration depth.

DETAILED DESCRIPTION OF THE INVENTION

Figure 4:
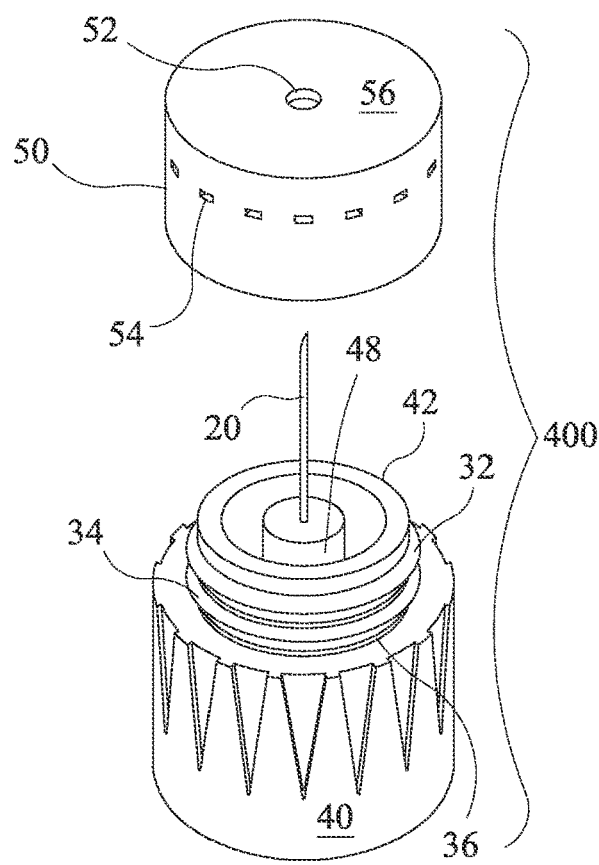
FIG. 4 is an exploded view of a needle-bearing hub with an audible and/or tactile penetration depth indication cup according to another embodiment of the invention.

As used herein, the "distal" direction is in the direction of the injection site, and the "proximal" direction is the opposite direction. The "axial" direction is along, or parallel to, the longitudinal axis of the syringe body. The cannula is generally arranged axially in a medication pen. "Radially" is a direction perpendicular to the axial direction. Thus, "radially inward" generally means closer to the needle. The accompanying figures are schematic and not to scale.

FIG. 1 is a cross section of a disposable pen needle 10 with a plastic non-patient end cannula 30. The plastic non-patient end cannula 30 may be molded as part of the hub 40, which is adapted for attachment to a medication pen, or the like, via threads 42 or other attachment means known in the art, such as cooperating detents and protrusions which snap together. The patient-end of the needle is a stainless steel cannula 20 with a single point (similar to a syringe needle) which can be attached to the hub 40 with an adhesive, such as a UV curable adhesive, spin welding or insert molding. Alternatively, the needle can be attached to the hub with a mechanical lock or other means known in the art.

Because the non-patient end cannula does not pierce the patient's tissue, it may be made with a larger inside and outside diameter, which makes the element stronger and more reliable for insertion into the medication compartment of a medication delivery device such as a medication pen where the non-patient end cannula pierces a septum of a medication cartridge. The non-patient end needle is not required to be the same gauge as the patient-end needle, and in fact the non-patient end of the needle is preferably larger than the patient end. Thus, a more stable piercing mechanism is provided. In embodiments, the patient end cannula is 33 gauge or smaller and the non-patient end needle is larger gauge.

The non-patient end needle, even if made of a lower modulus material, such as plastic, can be made sufficiently strong by increasing the outside diameter. An exemplary calculation of the inside and outside diameter based on the maximum buckling load for a preferred polypropylene plastic material is shown below. Such calculation is not to be deemed as limiting the invention:

| Elements | Unit | Formula | Calculations |
| --- | --- | --- | --- |
| Max Buckling Load | F (lb) | Fmax = $\pi^2$ EI/(KL)$^2$ | 1.501039677 |
| Constant | K | 2 | 2 |
| Moment of Inertia | I (in$^4$) | I = $\pi$(Dout$^4$ − Din$^4$)/64 | 1.161528E−07 |
| Cross Sectional Area | A (in$^2$) | A = $\pi$(Dout$^2$ − Din$^2$)/4 | 0.000883573 |
| Max Axial Stress | $\sigma$ (psi) | $\sigma$ = Fmax/A | 1698.8294 |
| Modulus of Elasticity/ Youngs Modulus | E (psi) | 213333 | 213333 |
| Length of Column | L (in) | 0.238 | 0.238 |
| Diameter | NP Cannula Dia (inches) | | |
| | Din | 0.03 | 0.03 |
| | Dout | 0.045 | 0.045 |
| Constant | Pi ($\pi$) | 3.141592654 | 3.141592654 |

The inner diameter of a non-patient end cannula according to the invention is preferably in a range of 0.002 to 0.100 inches. The outer diameter of the non-patient end plastic cannula is preferably in a range of 0.007 to 0.1000 inches. The patient end needle is preferably stainless steel with a sharpened bevel. The patient end needle may be, for example, 30 gauge, 31 gauge, 32 gauge, 33 gauge or even smaller. In the most preferred embodiment the patient end needle is insert molded with the non-patient end cannula.

When used with a medication pen, since a portion of the flow is through a larger diameter, the flow of medication can be increased, permitting lower thumb-button force and enabling the use of a small cannula for the injection end cannula.

FIG. 2 depicts the outside of a hub 40 according to the invention. In contrast to a conventional pen needle, where a protruding adhesive well is provided so that the cannula can be retained in a tubular structure on the hub, the patient-end needle according to the embodiment shown is received inside the non-patient end plastic cannula which may be insert molded directly with the hub, and is not required to be mounted on a protruding member. This permits the side 44 of the hub that is facing the patient to be flat and unobstructed during an injection.

FIG. 3 depicts the non-patient cannula, which in some embodiments is molded in one piece with the hub. As with the currently available designs, the non-patient end cannula preferably does not protrude beyond the plane formed by the edge surrounding the open proximal end of the hub 40.

FIG. 4 is an exploded view of an assembly 400 according to another embodiment of the invention, in which the pen needle provides an audible and/or tactile indication that injection depth has been achieved. In this view, hub 40 is provided with a central post 42 extending distally from the main body portion of the hub 40. In the embodiment shown, needle 20 is installed in an adhesive well 48 which protrudes from the hub radially inward of the post 42. The needle 20 is fixed in an axial position. It is not necessary to provide a gap between post 42 and adhesive well 48, and these can be formed with a flat patient-facing surface.

In the embodiment shown, post 42 is provided with a pair of radially projecting members 32, 34 forming parallel rings around the post 42. Each ring may be provided with an inclined surface sloping radially away from the patient end of the needle to facilitate the engagement of a cup 50 over the post 42 as described below. Projection 34 defines a recess 36 on the proximal side of the projection 34 and adjacent the wider main body portion of the hub 40.

Figure 5:
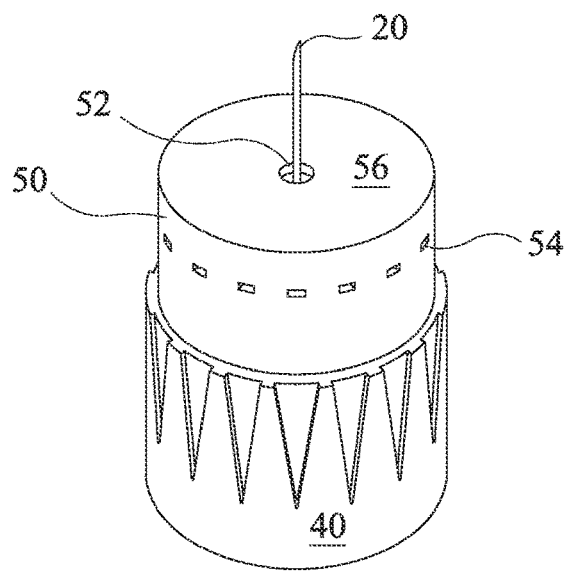
FIG. 5 is a view of the assembly of FIG. 4 with the cup installed on the hub.
Figure 9:
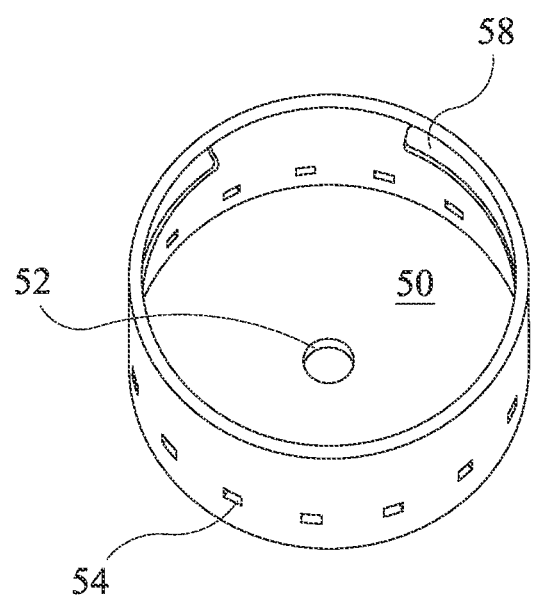
FIG. 9 is a perspective view of the inside of a cup according to one embodiment of the invention.

FIG. 5 depicts the cup received on the post. Needle 20 projects through hole 52 in the cup 50. The position of cup 50 shown in FIG. 5 is the furthest proximal position that can be achieved by the cup 50 with respect to the hub 40. This is the position reached at full injection depth, when the skin-contacting surface 56 contacts the patient's skin and the needle is at an optimal injection depth. An optimal patient end needle length is predetermined for the intended use of the medication delivery device, typically in the case of medication pen, an intradermal or subcutaneous injection.

The cup 50 has a sidewall extending in a proximal direction away from the skin contact surface 56. The sidewall is received around post 42. As shown in the cross sectional view of FIG. 7, an inwardly projecting member 58 on the proximal end of the sidewall of the cup engages the distal end of the projection 34 in a first position, shown in FIG. 7 and engages a recess 36 on the proximal side of the projection in a second position, as shown in FIG. 8. In a preferred embodiment, the inwardly projecting member forms a ring around the interior surface of cup 50. Other embodiments of the radially inward and outward members on the post and cup are within the scope of the invention. For example, a spiral channel may be provided on the hub, and a projection on the cup follows a helical path formed by the thread-like channel on the hub while the skin-contact surface 56 is pushed proximally. When the optimal penetration depth is achieved, a projection on the cup engages a recess in the hub like a hook. Other mechanisms known in the art may be used to provide an audible and/or tactile sensation when the cup is moved proximally. For example, one or more slots provided on the outside of the hub engaging with one or more protrusions on an interior surface of the cup would be an acceptable equivalent for the rings described above.

Preferably, the cup engages the hub so that the cup is not easily removed prior to injection, and prevented from movement in a distal direction after full injection depth is reached. In the position of FIG. 7, for example, prior to an injection, the cup 50 may be retained between projections 32 and 34 with an interference fit. Movement from the position of FIG. 7 to the position of FIG. 8 is accompanied by an audible and/or tactile indication as the inwardly projecting member 58 is received in recess 36. As the patient inserts the needle the tissue comes into contact with the skin-contacting surface 56 and forces it downward. This forces the cup to slide down the central post over the ring-shaped projection. The outwardly projecting member 34 on the post and the inwardly projecting member on the cup are sized so that a certain amount of force is required to overcome the resistance. Generally at least about 2 psi, and preferably above about 5 psi pressure must be applied to overcome the resistance to proximal movement of the cup. Creating an audible snap from this engagement requires a certain amount of elasticity in the cap, as understood by the person of ordinary skill in the art.

According to embodiments of the invention, the device provides a visual indication that full penetration depth has been achieved and that the pen needle has been used. As shown in FIG. 6, windows 54 are provided around the circumference of the cup toward the distal end. A color indicator band on the hub post which is not visible through the windows in the first position becomes visible in the second position. Conventional pen needles do not provide an indication that the pen needle has been used. The system according to the invention is expected to improve user compliance.

Figure 10:
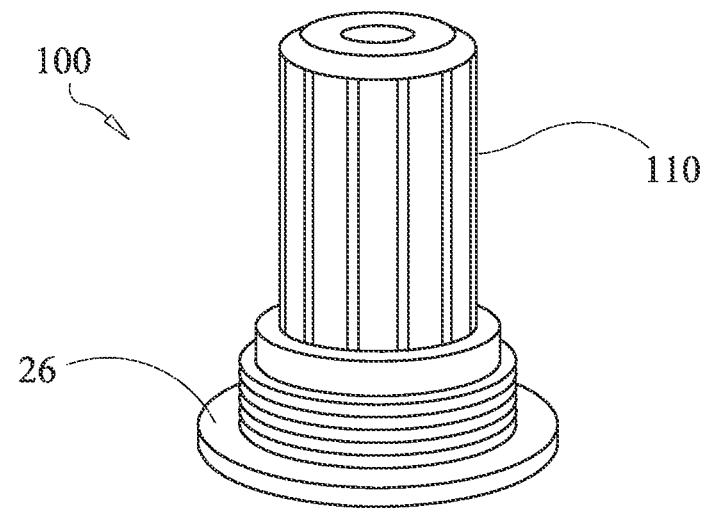
FIG. 10 depicts the needle assembly component of a two-piece hub according to another embodiment of the invention.

FIGS. 10 through 13 depict another embodiment according to the invention, wherein the conventional hub is replaced with a two-piece assembly. According to this embodiment of the invention, as shown in FIG. 10, disposable patient end needle assembly 100 is provided with a cap 110 which mates with base 26 to provide a sterile enclosure around the needle. The disposable pen needle assembly may be provided with a peelable sterile label, similar to the "teardrop label" provided with a disposable pen needle hub according to current and conventional design—except that the inventive needle assembly is smaller. Alternatively, a plastic lid over the end of the cap 110 may be used.

Figure 11:
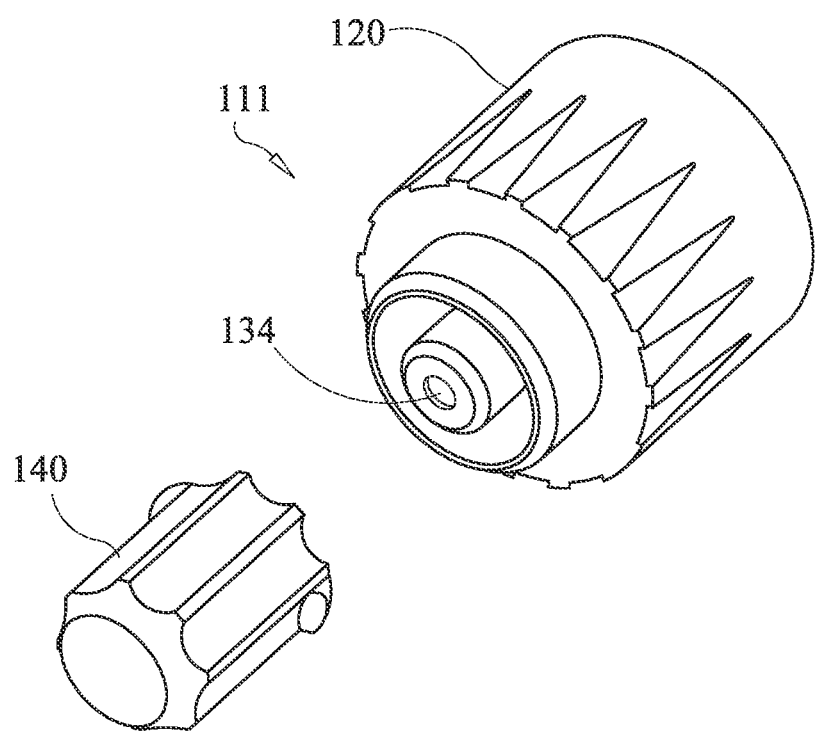
FIG. 11 depicts the adapter component of the two-piece hub with an adapter cover.
Figure 12:
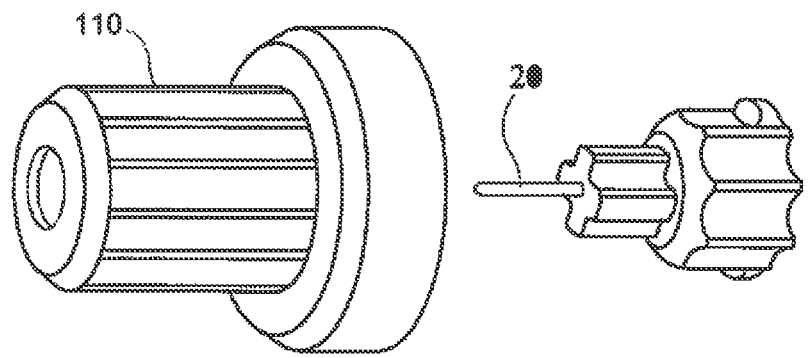
FIG. 12 depicts a two-piece hub assembly.
Figure 13:
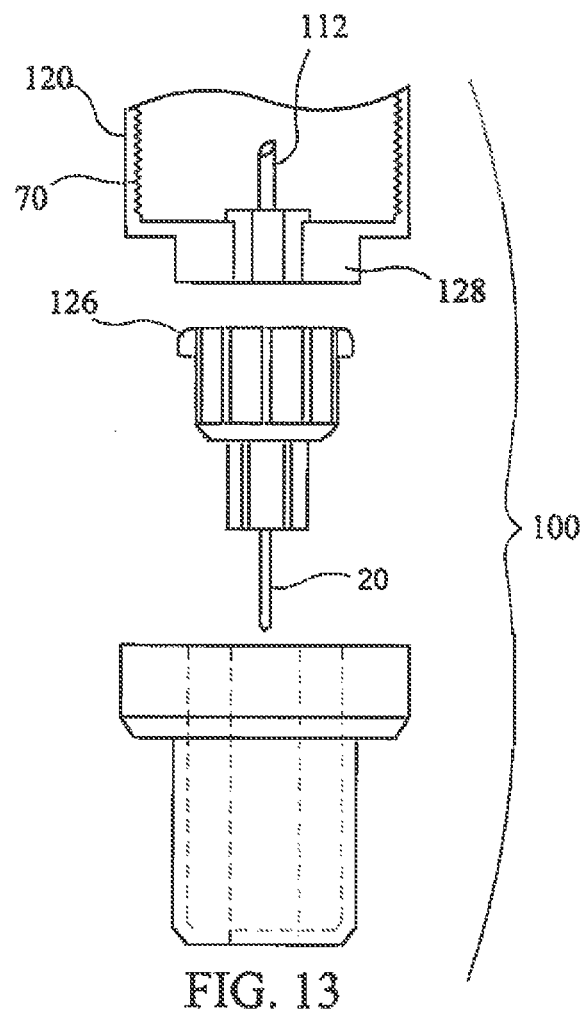
FIG. 13 is an exploded view of the two-piece hub assembly. Including the adapter, single use needle, and cover.

FIG. 11 and FIG. 13 depict adapter body 120 of an adapter 111 which is provided with threads 70 or other means for connecting to a medication delivery device such as a medication pen. The adapter 111 includes a proximal, non-patient end needle 112 for accessing the interior of the medication pen. In embodiments, non-patient end cannula 112 is plastic and may be molded in one piece with the adapter 111 as described above, reducing the number of beveled stainless steel parts required for the assembly. Attaching the adapter 111 to the medication pen pierces the septum of a medication pen cartridge. The distal or patient side of the adapter 111 includes a fitting 128 for mating with the needle assembly. In embodiments, the reusable adapter 111 is intended to remain on the medication pen for 10 to 30 uses, mirroring the usage pattern of the medication pen cartridge. Thus, the adapter 111 and the needle assembly may be packaged and sold separately if desired.

In embodiments, fitting 128 is provided with a custom taper surrounding orifice 134 of the adapter 111, providing fluid connection between the adapter 111 and the needle assembly 110. This arrangement is similar in principle to a miniature luer lock fitting on a syringe. The needle assembly may be provided with locking protrusions 126 to mate with the adapter fitting 128, for example. The orifice 134 may be provided with an adapter cap 140 which is installed after the needle is removed to prevent leakage. Alternatively, a valve or septum may be incorporated into the adapter to prevent leakage.

A primary advantage of the pen needle assembly according to the invention is the reduction in size of the disposable component. A commercial pen needle currently marketed has an outer volume on the order of 0.15 in$^3$. The disposable needle assembly will reduce this volume by at least one third, preferably by one half, and most preferably by two thirds. Thus, in the presently preferred embodiments, the volume of a needle assembly and cap according to the invention is expected to be as low as 0.10 in$^3$ and even as low as 0.05 in$^3$. The cost savings of using the two-part hub are realized in reduced packaging and reduced materials costs. Additionally, the consumer disposes of only the patient end needle when finished with an injection, reducing the amount of sharps to be disposed of.

In all of the foregoing embodiments, the parts of the pen needle according to the invention are preferably injection molded plastic except for the patient end needle. The parts described in the above two-part hub can be fabricated with less than 75 percent and preferably about 50 percent less volume of plastic than a current pen needle design.

The above description of the preferred embodiments is not to be deemed limiting of the invention, which is defined by the following claims. The foregoing description should provide the artisan of ordinary skill with sufficient information to practice variants of the embodiments described. Features described in connection with one embodiment or independent claim may be used in connection with another disclosed embodiment or another independent claim without departing from the scope of the invention.

The invention claimed is:

1. A pen needle providing at least one of an audible and tactile injection depth indication, comprising:
   a. a hub adapted for attachment to a medication pen body and having a central post extending distally from a main body portion of the hub, the main body portion of the hub being wider than the post, and having a needle fixed in an axial position on the post;
   b. the post having a radially outwardly projecting member and a recess adjoining the main body portion of the hub; and
   c. a cup radially situated around the post having a skin contact surface on a distal end thereof and a sidewall extending proximally from the skin contact surface, said sidewall having an inwardly projecting member engaging the outwardly projecting member on the post;
   d. the cup being movable from a first position, in which the inwardly projecting member is on a distal side of the outwardly projecting member on the post, to a second position, in which the inwardly projecting member on the cup engages the recess adjoining the main body portion of the hub;
   e. wherein the engagement of the inwardly projecting member on the cup and the recess adjoining the main body portion of the hub in the second position creates the at least one of the audible and tactile indication to indicate full penetration depth of the needle.

2. The pen needle according to claim 1, wherein the cup is mechanically engaged with the hub in the first and second positions to prevent movement in a distal direction.

3. The pen needle according to claim 2, further comprising:
   a. at least one window situated near the distal end of the cup; and
   b. a color indicator on the hub which is not visible through the window in the first position and is visible through the window in the second position.

4. The pen needle according to claim 1, further comprising:
   a. a plurality of windows situated around a circumference of the cup near the distal end of the cup; and
   b. a color indicator band on the hub which is not visible through the windows in the first position and is visible through the windows in the second position.

5. The pen needle according to claim 1, wherein the radially outwardly projecting member comprises a distal ring situated on a periphery of the post and a proximal ring parallel to the distal ring, with another recess formed between the distal and proximal rings.

6. The pen needle according to claim 1, wherein engagement between the outwardly projecting member on the post and the inwardly projecting member on the cup resists movement of the cup in a proximal direction at a force below about 2 psi.

* * * * *